US009241692B2

(12) United States Patent
Gunday et al.

(10) Patent No.: US 9,241,692 B2
(45) Date of Patent: Jan. 26, 2016

(54) PRESSURE/VACUUM ACTUATED CATHETER FORCEPS

(75) Inventors: Erhan H. Gunday, Great Neck, NY (US); Lawrence J. Gerrans, San Anselmo, CA (US)

(73) Assignee: SANOVAS, INC., San Rafael, CA (US)

( * ) Notice: Subject to any disclaimer, the term of this patent is extended or adjusted under 35 U.S.C. 154(b) by 946 days.

(21) Appl. No.: 13/096,388

(22) Filed: Apr. 28, 2011

(65) Prior Publication Data

US 2011/0270126 A1     Nov. 3, 2011

Related U.S. Application Data

(60) Provisional application No. 61/328,969, filed on Apr. 28, 2010.

(51) Int. Cl.
| | | |
|---|---|---|
| *A61B 10/00* | (2006.01) | |
| *A61B 10/04* | (2006.01) | |
| *A61B 10/02* | (2006.01) | |

(52) U.S. Cl.
CPC ............ *A61B 10/04* (2013.01); *A61B 10/0275* (2013.01)

(58) Field of Classification Search
CPC ............................ A61B 10/04; A61B 10/0275
USPC ............. 600/433–435, 585; 604/164.13, 523, 604/531
See application file for complete search history.

(56) References Cited

U.S. PATENT DOCUMENTS

| | | | |
|---|---|---|---|
| 3,289,669 A | | 12/1966 | Dwyer et al. |
| 3,590,808 A | | 7/1971 | Muller |
| 4,650,460 A | * | 3/1987 | Roizenblatt ............ 604/22 |
| 4,986,807 A | * | 1/1991 | Farr ....................... 604/22 |
| 5,335,671 A | * | 8/1994 | Clement ................. 600/566 |
| 5,980,546 A | * | 11/1999 | Hood ...................... 606/171 |
| 6,017,316 A | | 1/2000 | Ritchart et al. |
| 6,080,175 A | * | 6/2000 | Hogendijk .............. 606/185 |
| 6,251,121 B1 | * | 6/2001 | Saadat .................... 606/180 |
| 6,540,761 B2 | * | 4/2003 | Houser ................... 606/170 |

(Continued)

FOREIGN PATENT DOCUMENTS

EP        1785097 A2     5/2007

OTHER PUBLICATIONS

European Search Report; Application No. EP 11 30 5507; Issued: Aug. 18, 2011; 8 pages.

(Continued)

*Primary Examiner* — Rene Towa
(74) *Attorney, Agent, or Firm* — St Onge Steward Johnson and Reens LLC

(57) ABSTRACT

A method for extracting a tissue sample is provided, including the steps of inserting a catheter into a bodily cavity, the catheter having a sampling chamber, a movable cover, and an actuation mechanism for actuating the cover, positioning the sampling chamber next to tissue to be sampled, providing a fluid to the actuation mechanism to open the cover, supplying a vacuum to draw tissue sample into the sampling chamber and to close the cover, and withdrawing the catheter from the bodily cavity. Catheter forceps for obtaining a tissue sample are also provided, including a catheter, a sampling chamber positioned at a distal end of the catheter and having a movable cover, and an actuation mechanism for moving the movable cover to an opened position by providing a fluid to the actuation mechanism and to a closed position by providing a vacuum to the actuation mechanism.

26 Claims, 12 Drawing Sheets

(56) References Cited

U.S. PATENT DOCUMENTS

| | | |
|---|---|---|
| 7,297,121 B2 | 11/2007 | Turturro et al. |
| 7,351,210 B2 | 4/2008 | Cicenas et al. |
| 7,390,306 B2 | 6/2008 | Mark |
| 7,458,940 B2* | 12/2008 | Miller .......................... 600/568 |
| 2004/0087872 A1* | 5/2004 | Anderson et al. ............. 600/564 |
| 2005/0101880 A1* | 5/2005 | Cicenas et al. ................ 600/567 |
| 2006/0047219 A1* | 3/2006 | Baruti et al. .................. 600/564 |
| 2007/0213630 A1* | 9/2007 | Beckman et al. ............. 600/562 |
| 2008/0103411 A1* | 5/2008 | Van Bladel et al. ........... 600/564 |
| 2008/0300506 A1 | 12/2008 | McIntyre |
| 2009/0227893 A1* | 9/2009 | Coonahan et al. ............ 600/566 |
| 2010/0121270 A1 | 5/2010 | Gunday et al. |
| 2012/0226103 A1 | 9/2012 | Gunday et al. |

OTHER PUBLICATIONS

Office Action of the European Patent Office, Application No. 11305507.3, dated Feb. 6, 2015, 5 pages.

\* cited by examiner

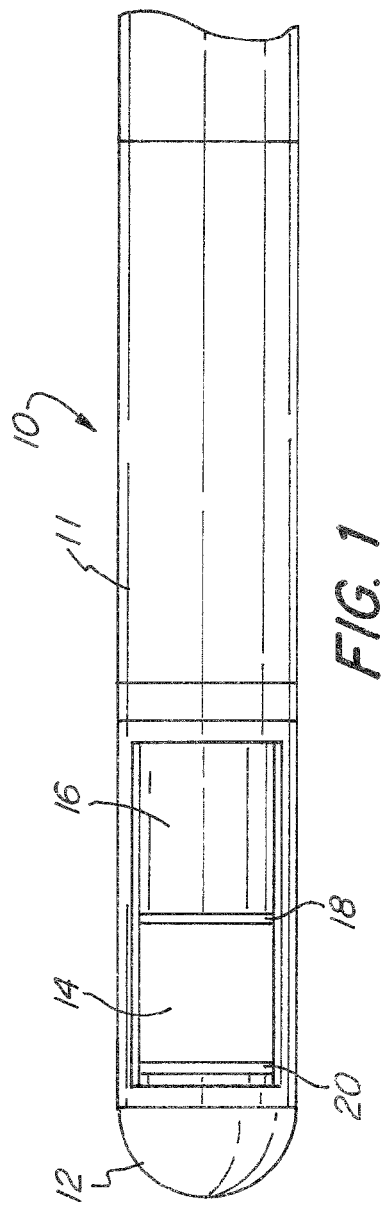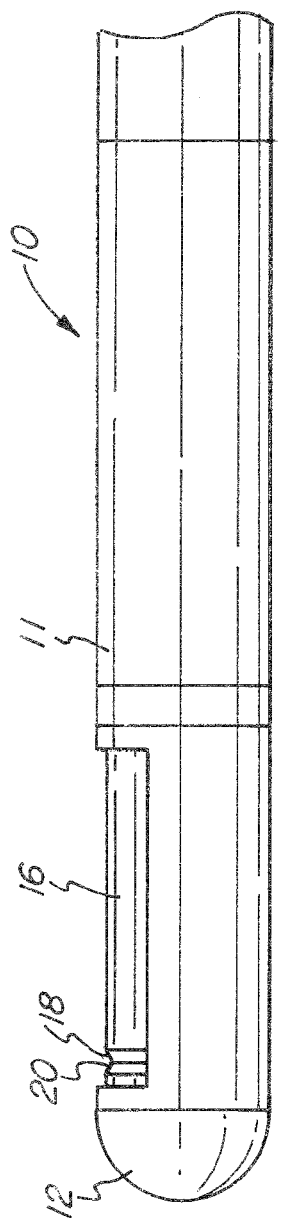

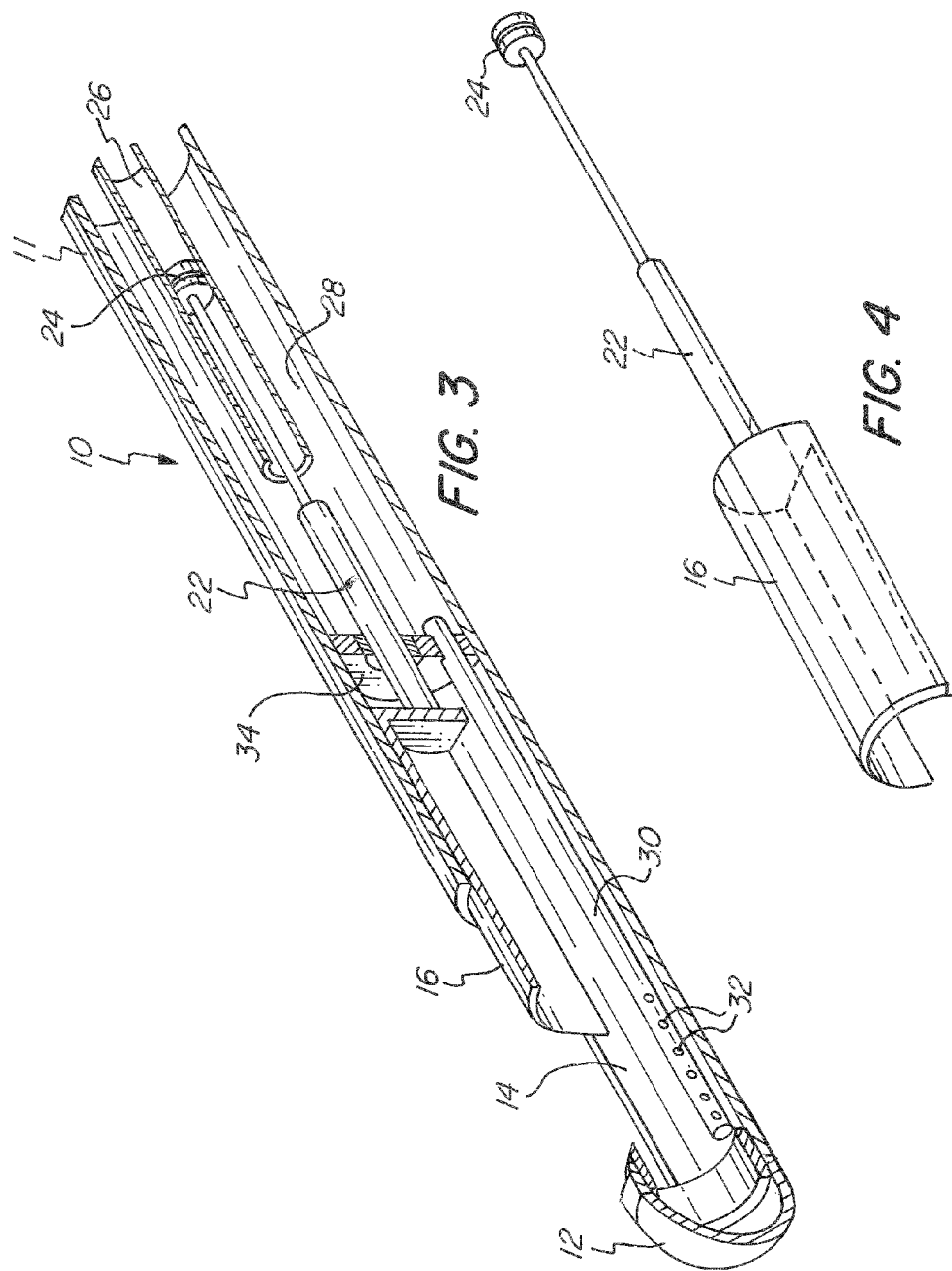

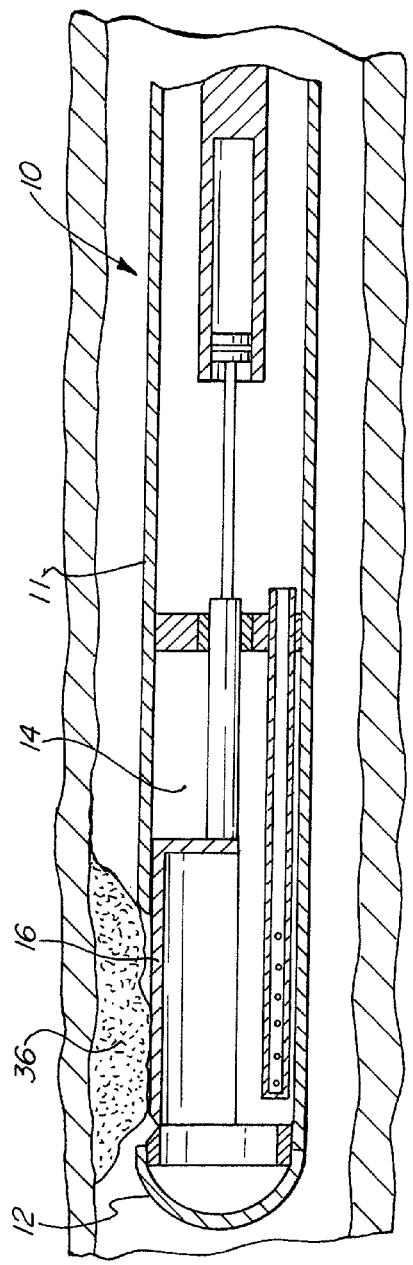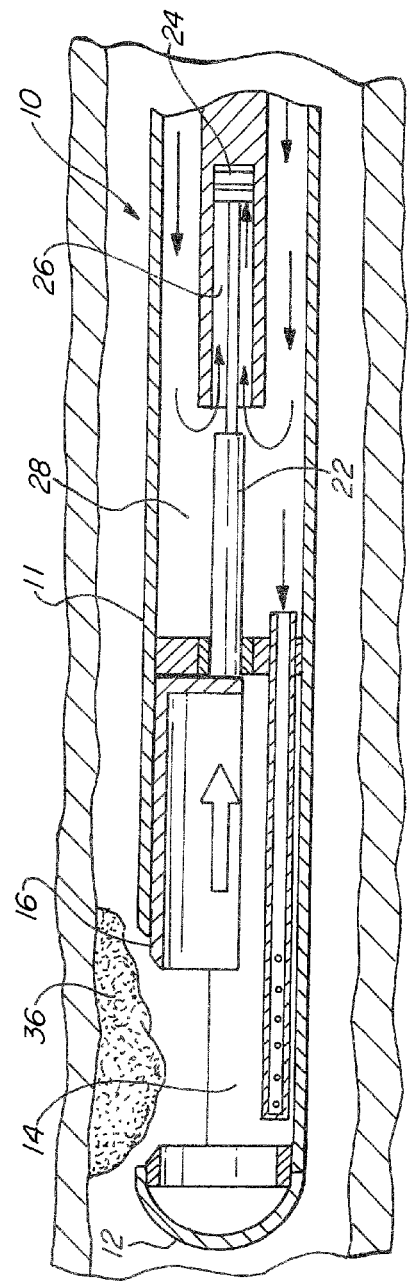

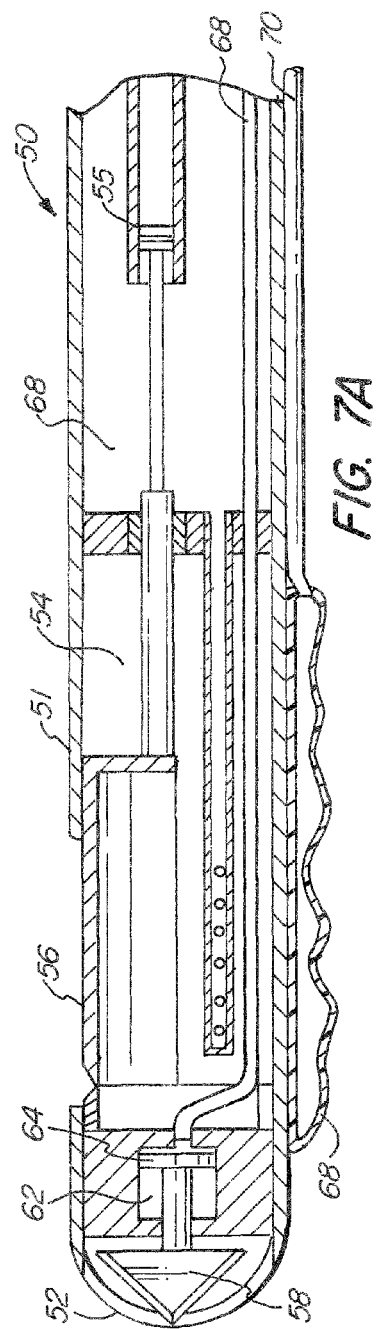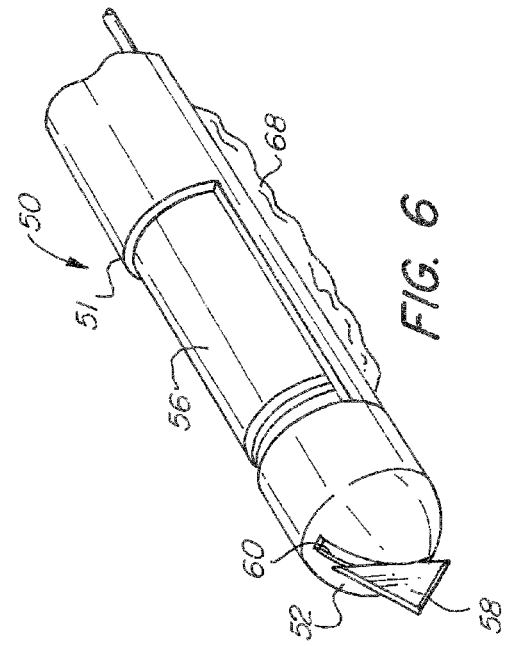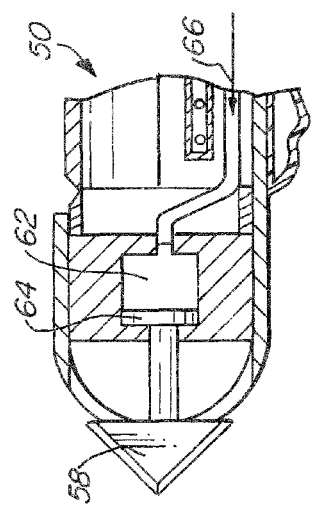

PRESSURE/VACUUM ACTUATED CATHETER FORCEPS

CROSS-REFERENCE TO RELATED APPLICATIONS

The present application claims the benefit under 35 U.S.C. §119(e) of the U.S. Provisional Patent Application Ser. No. 61/328,969 filed on Apr. 28, 2010, the content of which is incorporated herein by reference.

FIELD OF THE INVENTION

The invention relates to the field of medical diagnosis and treatment. More specifically, the invention relates to catheter forceps that are actuated by pressurized fluid and/or vacuum, and are adapted for tissue sampling and withdrawal for examination and analysis.

BACKGROUND OF THE INVENTION

Biopsy is a commonly performed medical procedure in which tissue samples are obtained for diagnostic purposes. Such a procedure typically includes cutting a tissue sample and then retrieving the sample from a patient's body.

Numerous types of biopsy forceps and devices have been developed for in vivo medical diagnosis and treatment of different conditions. Such devices are designed for sampling tissue within the body, such as may be performed, for example, in endoscopic, bronchoscopic, laparoscopic, vascular, neurologic and various other types of procedures, to retrieve biopsy samples for analysis and identification of tissue types.

The biopsy forceps and devices typically include small diameter swabbing sponges, coring needles and instruments with cutting jaws at a distal end that are operated remotely through an actuator positioned at a proximal end. The biopsy forceps and devices are typically carried on a distal end of an instrument, stick, syringe or catheter, and are positioned around a tissue portion selected for removal and diagnosis.

During a biopsy tissue sampling procedure, a physician first inserts a catheter portion into a portion of the patient's body from which the tissue sample needs to be taken. The physician then guides the catheter through a passageway, such as a blood vessel, until the biopsy instrument of choice is positioned by a tissue sample site. Next, the physician swabs the surface of the site, inserts the needle into the site and removes a core sample from the site. Alternatively, the physician opens the jaws of the forceps, positions the jaws around the tissue to be sampled, and manipulates the actuator so that the jaws close around the tissue. A sample of the tissue is cut from the biopsy site while it is trapped between the jaws or picked up by other means. Keeping the jaws closed, the physician withdraws the biopsy forceps and opens the jaws to collect the tissue sample.

Several biopsy devices have been proposed. For example, U.S. Pat. No. 3,590,808 to Muller describes a biopsy tool that includes a rigid tip for collection of a tissue sample attached to a flexible tube, such as a catheter. The rigid tip includes a knife for cutting off the tissue samples. The knife is advanced forward to cut off the tissue sample by supplying air under positive pressure from a syringe via a first duct, and is then retracted by supplying air under negative pressure from the syringe. The tool also includes a radial cavity for capturing the severed tissue. Vacuum is supplied to the radial cavity through a separate duct to draw the tissue sample into the cavity.

However, the known biopsy tools suffer from a number of disadvantages and shortcomings. For example, the prior art biopsy forceps and devices are typically limited to taking a single tissue sample, after which the device may be withdrawn from the patient's body and the tissue collected before the device can be used again to take a second tissue sample. Accordingly, it is a major disadvantage of the existing art to take sufficient sample quantities in an expeditious manner. An additional disadvantage of prior art devices is that it is often very difficult to accurately position the forceps next to the tissue to be sampled. Yet another disadvantage of prior art devices is that the samples are not immediately captured and securely held in a container at the sample site.

Hence, there is a significant need for a forceps device that is capable to taking multiple tissue samples while in the patient's body without the need of withdrawing the device and removing the collected tissue sample before another sample can be collected. There is also a need for a forceps device that can be precisely positioned next to the tissue to be sampled. There is also a need for a forceps device that can be precisely positioned and actuated to sample indirect tissues, such as those positioned beyond the walls of an airway, lumen or vessel. Furthermore, there is a need for a repetitively actuated forceps device that can be precisely operated, such that its insertion, actuation, depth and repetition cycles are be known and controlled. There is further a need to provide a forceps device that is capable of immediately capturing and securely holding a tissue sample in a container at the sample site. Additionally, there is a need for a forceps device that can be placed and actuated under direct and/or indirect visualization.

SUMMARY OF THE INVENTION

Accordingly, it is an object of the present invention to provide a catheter forceps for extracting a tissue sample that is capable of taking multiple tissue samples while in the patient's body.

It is also an object of the present invention to provide a catheter forceps for extracting a tissue sample that can be precisely positioned next to the tissue to be sampled.

It is a further object of the present invention to provide a catheter forceps for extracting a tissue sample that is capable of immediately capturing and securely holding a tissue sample in a sampling chamber at the sample site.

It is also an object of the present invention to provide a catheter forceps for extracting a tissue sample that is capable of being precisely positioned and actuated to sample indirect tissue samples, such as those positioned beyond the walls of an airway, lumen or vessel. An exemplary embodiment of such capability is to facilitate a transbronchial sampling of a lymph node tissue.

It is a further object of the present invention to provide a repetitively actuated catheter forceps for extracting tissue samples that can be precisely operated, such that its insertion, actuation, depth and repetition cycles are be known and controlled.

Additionally, it is a further object of the present invention to provide a repetitively actuated catheter forceps for extracting tissue samples using direct and/or indirect visualization methods, alone or in combination, such as the deployment of the biopsy forcep under bronchoscopic visualization in concert with fluoroscopic or ultrasound localization to facilitate the transbronchial biopsy of a specific lymph node.

In order to overcome the deficiencies of the prior art and to achieve at least some of the objects and advantages listed, the invention comprises a method for extracting a tissue sample, including the steps of inserting a catheter into a bodily cavity, the catheter having a sampling chamber, a movable cover, and an actuation mechanism for actuating the movable cover, positioning the sampling chamber next to tissue to be sampled, providing a fluid to the actuation mechanism to open the movable cover, supplying a vacuum to draw tissue sample into the sampling chamber and to close the movable cover, and withdrawing the catheter from the bodily cavity. In some embodiments, the process is repeated at least once before the catheter is withdrawn from the bodily cavity.

In some embodiments, the catheter has a lumen in fluid communication with both the actuation mechanism and the sampling chamber for providing at least one of a fluid and a vacuum to the actuation mechanism and the sampling chamber.

In certain embodiments, the method further includes the step of cutting into the tissue to be sampled by actuating a cutting device positioned at the distal end of the catheter by providing at least one of a fluid and a vacuum. In some of these embodiments, the cutting device has an actuator, the step of cutting into tissue includes supplying a fluid to the actuator to position the cutting device in an activated position, in which the cutting device extends beyond the distal end of the catheter, and the method further includes the step of positioning the cutting device in an inactivated position, in which the cutting device does not extend beyond the distal end of the catheter, by supplying a vacuum to the actuator. In additional embodiments, the catheter has a first lumen in fluid communication with both the actuation mechanism and the sampling chamber, and the at least one of a fluid and a vacuum is provided via a second lumen in the catheter in fluid communication with the actuator.

In some of the above embodiments, the cutting device has an actuator, the step of cutting into tissue comprises providing a vacuum to the actuator to position the cutting device in an activated position, in which the cutting device extends beyond the distal end of the catheter, and the method further comprises the step of positioning the cutting device in an inactivated position, in which the cutting device does not extend beyond the distal end of the catheter, by supplying a fluid to the actuator. In certain of those embodiments, the at least one of a fluid and a vacuum is provided to the actuator of the cutting device via a lumen in fluid communication with the actuator, the actuation mechanism and the sampling chamber.

In certain embodiments, the method further includes the step of inflating at least one inflatable balloon provided on an outer wall of the catheter opposite the sampling chamber to position the sampling chamber adjacent to the tissue to be sampled. In some of these embodiments, the step of inflating the at least one inflatable balloon includes supplying a fluid thereto via a second lumen in the catheter.

In some embodiments, the steps of applying vacuum and providing fluid are controlled via a control device provided at a proximal end of the catheter.

In certain embodiments, the steps of applying vacuum and providing fluid are performed by a pump in fluid communication with the lumen in the catheter.

In some embodiments, the method further includes the step of opening the movable cover after the catheter is withdrawn from the bodily cavity to retrieve the tissue sample from the sampling chamber.

Catheter forceps for extracting a tissue sample are also provided, including a catheter, a sampling chamber positioned at a distal end of the catheter and having a movable cover, and an actuation mechanism for moving the movable cover to an opened position by providing a fluid to the actuation mechanism and to a closed position by providing a vacuum to the actuation mechanism.

In certain embodiments, the catheter has a lumen in fluid communication with both the actuation mechanism and the sampling chamber for providing at least one of a fluid and a vacuum to the actuation mechanism and the sampling chamber. In some of these embodiments, the lumen supplies a vacuum to the sampling chamber to draw tissue sample into said sampling chamber.

In some embodiments, the actuation mechanism has a piston positioned in an actuation chamber, and the actuation chamber is in fluid communication with the lumen.

In certain embodiments, fluid is supplied by a fluid source in fluid communication with the lumen. In some of these embodiments, the fluid source further includes a vacuum source. In other of these embodiments, the fluid source is an electro-pneumatic pump.

In some embodiments, the fluid is a gas.

In certain embodiments, the catheter forceps further includes at least one inflatable balloon positioned on an outer wall of the catheter opposite the sampling chamber. In some of these embodiments, the catheter has a first lumen in fluid communication with both the actuation mechanism and the sampling chamber, and a second lumen in fluid communication with the at least one inflatable balloon for supplying fluid thereto.

In some embodiments, the catheter forceps further includes a movable cutting device positioned at the distal end of the catheter. In certain of these embodiments, the cutting device has an actuator for moving the cutting device to an active position, in which the cutting device extends beyond the distal end of the catheter, and to an inactive position, in which the cutting device does not extend beyond the distal end of the catheter, by providing at least one of a fluid and a vacuum.

In some of the above embodiments, the catheter has a lumen in fluid communication with the actuation mechanism, the sampling chamber, and the actuator of the cutting device. In other of the above embodiments, the catheter has a first lumen in fluid communication with both the actuation mechanism and the sampling chamber, and a second lumen in fluid communication with the actuator of the cutting device.

In some of the above embodiments, the catheter and the forceps include direct and/or indirect markings to enable direct and/or indirect visualization of the device.

In some embodiments, the catheter forceps is controlled by an apparatus that monitors and precisely controls various aspects of the forceps' operation, such as its insertion depth, actuation and cycles of repetition.

In some of the above embodiments, the catheter forceps is navigated via direct and/or indirect visualization methods to facilitate sampling of indirect tissues, such as a transbronchial sampling of a lymph node tissue. In such embodiments, the biopsy forceps is deployed under bronchoscopic visualization in concert with fluoroscopic or ultrasound localization to facilitate the transbronchial biopsy of a specific lymph node.

Other objects of the invention and its particular features and advantages will become more apparent from consideration of the following drawings and accompanying detailed description.

BRIEF DESCRIPTION OF THE DRAWINGS

FIG. 1 is a top view of a pressure/vacuum actuated catheter forceps according to an exemplary embodiment of the present invention.

FIG. 2 is a side view of the pressure/vacuum actuated catheter forceps of FIG. 1.

FIG. 3 is a perspective cross-sectional view of the pressure/vacuum actuated catheter forceps of FIG. 1.

FIG. 4 is a perspective view of a cover of the pressure/vacuum actuated catheter forceps of FIG. 1.

FIGS. 5A-5D are cross-sectional views of the pressure/vacuum actuated catheter forceps of FIG. 1 being operated in a bodily cavity.

FIG. 6 is a perspective view of an exemplary embodiment of a pressure/vacuum actuated catheter forceps of the present invention.

FIGS. 7A and 7B are cross-sectional views of the pressure/vacuum actuated catheter forceps of FIG. 6, showing a cutting device in activated and inactivated positions.

DETAILED DESCRIPTION OF THE INVENTION

Figure 5C:
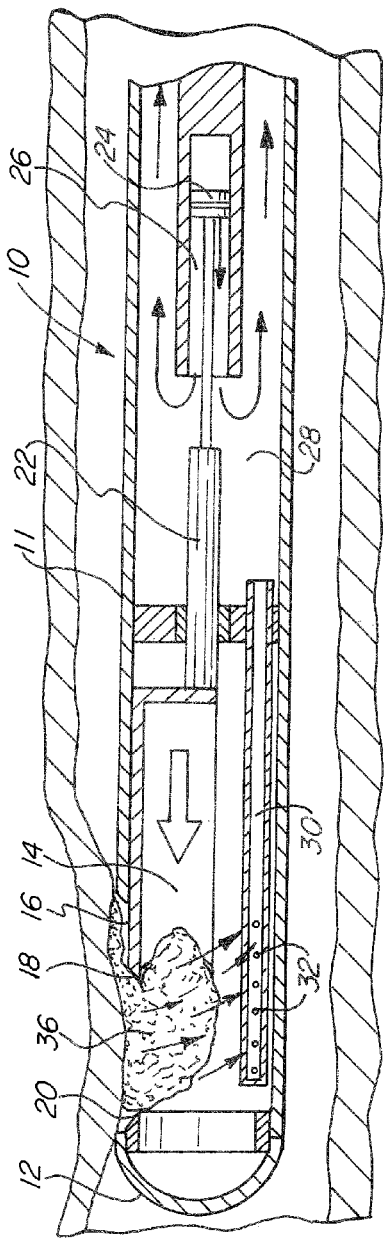

The basic components of one embodiment of a pressure/vacuum actuated catheter forceps in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

The pressure/vacuum actuated catheter forceps of the present invention may be used with various catheter devices, as well as various types of flexible and rigid endoscopes that include suitable working channels to quickly and efficiently obtain tissue samples from inside the body for pathological examination. If desired, the pressure/vacuum actuated catheter forceps can be made as a single use disposable unit provided in a sterile package at a very low cost.

In an advantageous embodiment, the catheter forceps are used with a steerable catheter system described in U.S. Patent Publication No. 2012/0226103, the disclosure of which is incorporated by reference herein in its entirety. The pressure/vacuum actuated catheter forceps can also be used with conventional instruments such as endoscopes that have suitable working channels.

An exemplary embodiment of the pressure/vacuum actuated catheter forceps of the present invention is illustrated in FIG. 1. The catheter forceps (10) include a catheter (11) with a distal tip (12). A proximal end of the catheter (11) is connected to a control device, such as a hand piece, described in more detail below. The catheter (11) is preferably made of any suitable material that is sufficiently flexible to facilitate introduction of the catheter forceps (10) into the patient's body through the working channels of the endoscopes or guiding catheters. The catheter can have any suitable length, depending on the particular application for which the forceps are being used. The outer diameter of the catheter (11) should usually be made as small as possible.

The catheter (11) can be pre-formed into many different shapes and can be used with various additional devices. In some embodiments, the catheter (11) may be coupled with an imaging system, e.g. a fiber optic image bundle, for imaging of the surrounding area during the introduction of the catheter forceps (10) into the patient's body. Two separate bundles, one for illumination and the other for imaging can also be used. It should be noted that other sources of illumination and/or imaging may also be employed. It should also be noted that the image sensor and/or illumination source can be located at the tip of the catheter forceps (10), eliminating the need for a coherent imaging fiber bundle, thus increasing image quality and reducing cost.

In certain advantageous embodiments, the catheter (11) includes imaging markers, such as radio opaque rings, located throughout the length of, or at or near, the distal tip (12). Such markers can be selected and appropriately positioned in order to reflect the relevant waves of various imaging modalities (e.g., x-ray) in order to allow the use of such modalities to assist with the precise positioning of the catheter forceps (10) inside a bodily cavity, as further discussed below.

The distal tip (12) is made out of a material suitable for medical applications, such as plastic or metal. For example, a range of polymers can be used for the construction of the distal tip, such silicone rubber, latex, or thermoplastic elastomers. Likewise, any suitable type of a metal, such as stainless steel, may be used.

The distal tip (12) of the catheter forceps (10) may come in a variety of sizes and diameters, which can be selected to suit the particular application for which the forceps are being used. This variety of available distal tip sizes allows the catheter forceps to be used in bodily cavities of various diameters and dimensions, such as large and small bronchial branches, sinuses, and vessels, having different types of tissues to be sampled. In certain advantageous embodiments, the outer diameter of the distal tip (12) may be 1 mm or less.

The distal tip (12) of the catheter forceps (10) may also come in a variety of shapes. In an exemplary embodiment shown in FIG. 1, the distal tip (12) has a rounded shape adapted to provide an easy passage through the working channel(s) of the various guiding catheters and/or endoscopes used to deploy the forceps (10).

The distal tip (12) can also include an access opening, through which a cutting device can be extended when the forceps (10) are actuated, such that the forceps can easily cut into the tissue from which a tissue sample is to be obtained. Any suitable cutting device, such as, for example, a sharp edge knife, may be used, depending on a type of the tissue to be sampled. The structure and operation of the cutting device is further described below.

The catheter forceps (10) further include a sampling chamber (14) positioned at the distal end of the forceps (10) for capturing and retaining a tissue sample. The sampling chamber (14) includes a movable cover (16), which is adapted to be opened and closed, capturing the tissue sample within the sampling chamber (14). The sampling chamber (14) typically remains closed during deployment of the forceps (10) through a working channel of a guiding catheter or an endoscope until it reaches the target tissue. The sampling chamber (14) can have any suitable shape and size depending on a particular application. It is desirable that the shape of the cover (16) is such that the volume of sampling chamber (14) is maximized for capturing larger tissue samples.

As shown in FIG. 2, the distal end of the movable cover (16) preferably includes a sharpened edge (18) that functions as a cutting device for resecting the tissue sample. A distal end of the sampling chamber (14) also preferably has a sharpened edge (20) corresponding to the sharpened edge (18) of the movable cover (16) such that the tissue sample is resected by both sharp edges (18) and (20) as the movable cover (16) is moving to a closed position. This way, when the movable cover (16) is moving forward, it is closing the specimen chamber (14) while simultaneously cutting the tissue and capturing the tissue sample within the chamber.

In some cases, the tissue to be sampled is removed by a device other than the catheter forceps (10), such as a resecting surface molded in or affixed to a balloon of a resector balloon system, as is described in U.S. patent application Ser. No. 12/269,495, the disclosure of which is incorporated by reference herein in its entirety. In certain embodiments, the distal edge of the chamber (14) may include a fixedly positioned sharp edge knife (not shown) that aids in cutting of the tissue to be sampled. When the sampling chamber (14) is closed, the sharp edge knife is not exposed, so that the catheter forceps (10) may be safely introduced into the patient's body.

The cover (16) moves forward and backward when it is activated with pressurized fluid (e.g., air) and/or vacuum. There is no electrical connection required to actuate the forceps (10), which enhances the safety of the device when it is introduced into the patient's body. Additionally, because the actuation of the forceps (10) does not require the use of electrical wires, the catheter (11) can have a very small diameter, which facilitates the introduction of the shaft into a body cavity.

As shown in FIG. 4, the movable cover (16) is connected to an actuation mechanism for moving the movable cover between opened and closed positions. The actuation mechanism includes a rod (22) connected to a piston (24). The piston (24) is slidably disposed in an actuation chamber (26), as illustrated in FIG. 3. The actuation chamber is in fluid communication with a lumen (28) provided in the catheter (11). The lumen (28) is used to provide a fluid and a vacuum to the actuation mechanism to actuate the movable cover (16). The lumen (28) is also in fluid communication with the sampling chamber (14) via a lumen (30). The lumen (30) has a plurality of holes (32) through which a vacuum is provided to the sampling chamber (14) via the lumen (28). The actuation mechanism is retained inside the catheter by a holder (34), which also functions to separate the sampling chamber (14) from the lumen (28).

FIGS. 5A-5D illustrate a stepwise actuation of the catheter forceps during the biopsy procedure. The catheter forceps (10) are primed with the sampling chamber cover (16) in the closed position. Then, the catheter forceps are introduced into a bodily cavity via a suitable catheter or endoscope device and are positioned next to the target tissue (36) to be sampled, as shown in FIG. 5A. Next, a pressurized fluid is supplied to the lumen (28) of the catheter (11) via a fluid source. The pressurized fluid enters the actuation chamber (26) and causes the piston (24) together with the attached rod (22) to move toward the proximal end of the catheter (11), as illustrated in FIG. 5B. This, in turn, causes the movable cover (16) to open.

Figure 5D:
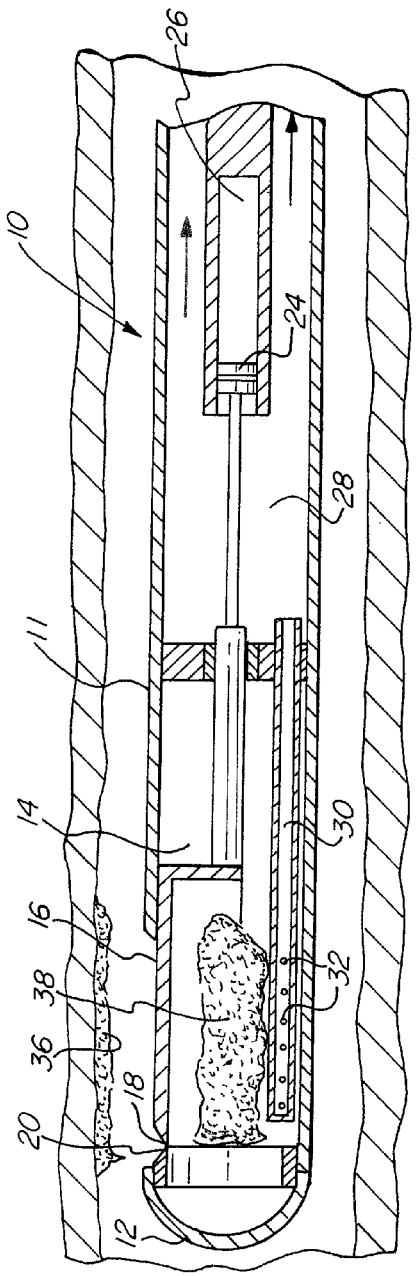

After the cover (16) is completely opened, the supply of pressurized fluid is terminated and a vacuum is provided to the lumen (28) from the fluid source, as shown in FIGS. 5C-D. The vacuum is established in the sampling chamber (14) via the lumen (30) and through the plurality of openings (32). The established vacuum in the sampling chamber (14) draws the tissue sample (38) into the chamber and aids in retention of the tissue sample inside the chamber (14). At the same time, the vacuum is provided to the actuation chamber (26) via the lumen (28), which causes the piston (24) with the attached rod (22) to move toward the distal end of the catheter (11). This movement of the piston and the rod causes the cover (16) to gradually close, thereby cutting off the tissue sample (38) by the sharpened edges (18, 20) of the cover and the sampling chamber. As the tissue sample (38) is being resected, it is retained in the sampling chamber (14) by the continuous supply of vacuum through the lumen (30).

Once the cover (16) is completely closed and the tissue sample (38) is enclosed inside the sampling chamber (14), the catheter forceps (10) may be withdrawn from the patient's body through the same catheter/endoscope lumen. After the catheter forceps (10) are withdrawn, the pressurized fluid is again supplied to the actuation mechanism via the lumen (28) to open the cover (16) and to retrieve the tissue sample (38) from the sampling chamber (14) for analysis.

The catheter forceps of the present invention may include various cutting devices to assist in positioning the forceps adjacent to the target tissue. For example, as shown in FIG. 6, the catheter forceps (50) includes a cutting device (58) positioned at the distal end (52) of the forceps and slidably attached to the catheter (51). The cutting device is extended into an activated position, in which the cutting device (60) extends beyond the distal end (52) of the catheter (51) through an opening (60) provided at the distal end of the catheter, as shown in FIG. 6. The cutting device (58) can be made with any suitable material and can have any suitable shape. In the embodiment shown in FIG. 6, the cutting device (58) has a triangular shape with a sharp side edges that facilitate cutting into the surrounding tissue.

As shown in FIGS. 7A and 7B, the cutting device (58) is actuated by an actuation mechanism comprising an actuation chamber (62) and a piston (64) slidably arranged inside the chamber (62) and coupled to the cutting device (58). The cutting device is actuated by providing at least one of a fluid and a vacuum to the actuation chamber (62) via a lumen (66) fluidly connected to the fluid source, such as a pump. In the embodiment shown in FIGS. 7A and 7B, the lumen (66) is fluidly isolated from the lumen (28) that supplies fluid/vacuum to the sampling chamber (54) and to the actuation mechanism (55) that actuates the movable cover (56). It should be noted that in other embodiments, fluid/vacuum can be supplied to the cutting device (58), the sampling chamber (54) and the movable cover (56) via the same lumen in the catheter (51). This can be accomplished, for example, by extending lumen (30) to a portion of the actuation chamber (62), either proximal or distal of the piston (64), as appropriate.

To actuate the cutting device (58), a pressurized fluid is supplied to the actuation chamber (62) from the fluid source via the lumen (66). As the pressurized fluid fills the chamber (62), it pushes the piston (64) toward the distal end of the catheter (51), which causes the cutting device (58) to extend out of the opening (60) at the distal end of the catheter (51), as shown in FIG. 7B. Once the cutting device (58) is placed into this activated position, the catheter (51) is pushed forward into the target tissue, such that the cutting device cuts into the tissue to aid positioning of the catheter forceps closer to the target tissue to be sampled. The cutting device can also assist in resecting the tissue sample to be captured in the sampling chamber (54).

Once the catheter forceps (50) are positioned at the target site and the tissue sampled is obtained, the cutting device (58) is positioned into the inactivated position, in which the cutting device (58) does not extend beyond the distal end of the catheter (51), as illustrated in FIG. 7A. This is achieved by providing vacuum from the fluid source to the actuation chamber (62) via the lumen (66) to pull the piston (64) toward the proximal end of the catheter, which in turn brings the cutting device (58) inside the catheter housing. It should be noted that, in appropriate configurations, vacuum can be applied to move the cutting device (58) into an activated position, and pressurized fluid can be supplied to move the cutting device (58) into an inactivated position. Once the cutting device (58) is positioned into the inactivated position, the catheter forceps (50) can be safely withdrawn from the patient's body.

In one advantageous embodiment, the catheter forceps of the present invention further includes an inflatable device to facilitate positioning of the forceps in larger bodily cavities, such as lung passageways. As shown in FIG. 6, the catheter (51) includes an inflatable balloon (68) positioned on the outer wall of the catheter. In the exemplary embodiment of the present invention shown in FIG. 6, the inflatable balloon (68) is positioned opposite the sampling chamber cover (56). However, the inflatable balloon (68) can be positioned at any other suitable location along the catheter. Additionally, a plurality of inflatable balloons can be positioned at different locations along the catheter (51) to further facilitate maneuvering and positioning of the catheter forceps inside a bodily cavity. The inflatable balloon(s) can also be used as a tamponade to control and/or stop bleeding from the tissue. The bleeding is tamponaded by inflating the inflatable balloon to create compression.

The inflatable balloon is inflated by supplying fluid thereto from the fluid source via a lumen (70). In the embodiment shown in FIG. 7A, the lumen (70) is separate from the lumens (28) and (66) that are used to supply fluid/vacuum to the sampling chamber (54), the movable cover (56) and the cutting device (58). However, it should be noted that, in some embodiments, the fluid can be supplied to the inflatable balloon (68), the sampling chamber (54), the cover (56) and/or the cutting device (58) via a single lumen. Further, to deflate the balloon (68), vacuum is provided to the balloon via the lumen (70) from the fluid source.

Figure 8:
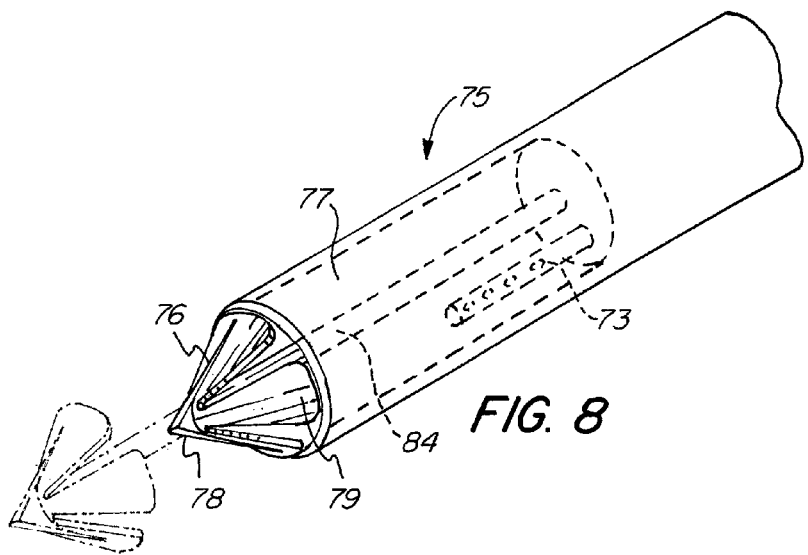
FIG. 8 is a perspective view of an exemplary embodiment of a pressure/vacuum actuated catheter forceps of the present invention.

The cutting devices used with the catheter forceps of the present invention can have various shapes and functions. For example, as shown in FIG. 8, the cutting device (76) has an anchor-like shape, with a sharpened distal end (78) and four paddles (79). The cutting device (76) is coupled to an actuation mechanism (84), such as a piston, which in turn is fluidly connected to a fluid/vacuum source. The cutting device (76) is actuated by supplying at least one of fluid and vacuum to the actuation mechanism (84) to position the cutting device (76) into an active position, as shown in phantom lines in FIG. 8. Then, the catheter forceps (75) is pushed into the tissue to be sampled, such that the sharpened distal end (78) of the cutting device (76) cuts into the tissue. As the forceps (75) is moved further into the tissue, the tissue collapses around the paddles (79). Next, the cutting device is retracted back into the forceps housing by supplying at least one of fluid and vacuum to the actuation mechanism (84). As the cutting device (76) is retracted, the paddles (79) scoop the tissue sample and draw is back into the sampling chamber (77) provided at the distal end of the catheter. The sampling chamber (77) typically includes a lumen (73), which fluidly couples the chamber (77) with a fluid source. As the tissue sample is drawn into the sampling chamber (77), vacuum is supplied to the chamber (77) via the lumen (73) to further facilitate capture and retention of the tissue sample in the chamber. In the embodiment shown in FIG. 8, the movable cover provided on the side of the sampling chamber may be eliminated such that the tissue sample is drawn into the sampling chamber (77) only from the distal end of the catheter.

Figure 9:
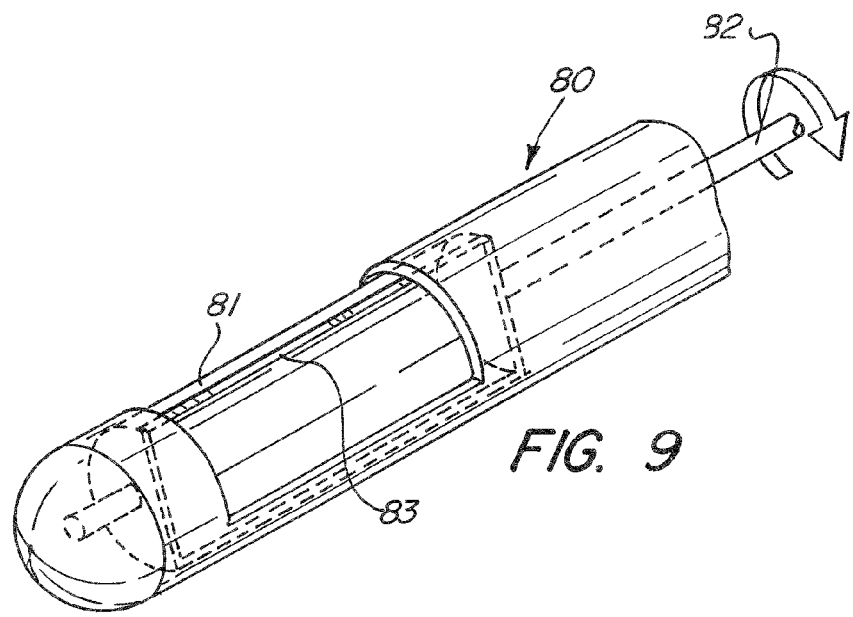
FIG. 9 is a perspective view of an exemplary embodiment of a pressure/vacuum actuated catheter forceps of the present invention.

In other advantageous embodiment, such as shown in FIG. 9, the sampling chamber cover (81) has a cylindrical shape with a sharpened edge (83) extending along the longitudinal axis of the cover. The cover is coupled to an actuation mechanism, such as a rod (82). Once the sampling chamber is positioned next to the tissue to be sampled, the cylindrical cover (81) is rotated around its longitudinal axis, shown by an arrow in FIG. 10, via the rod (82) such that the tissue sample is cut off and captured inside the sampling chamber. The cover (81) is actuated manually by rotating the rod (82) or pneumatically by supplying fluid and/or vacuum to any suitable pneumatic mechanism.

Figure 10:
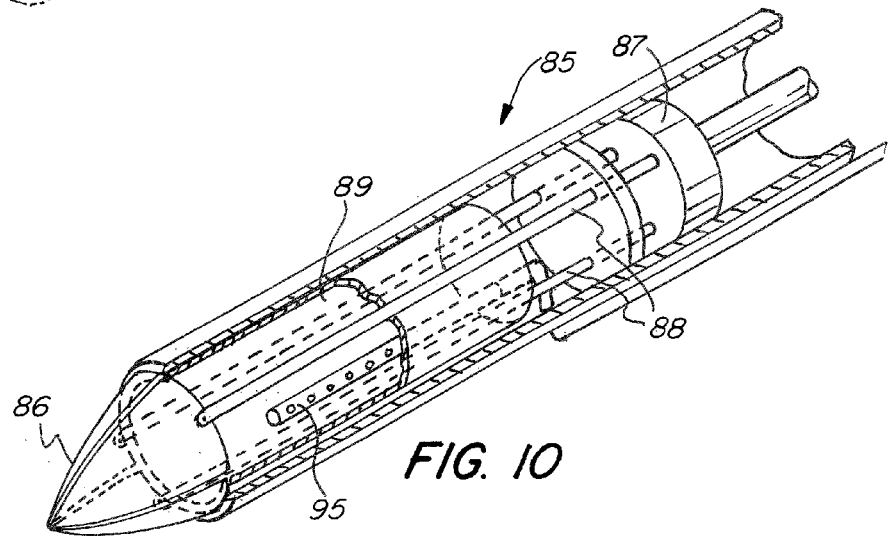
FIG. 10 is a perspective view of an exemplary embodiment of a pressure/vacuum actuated catheter forceps of the present invention.

The sampling chamber cover with the cutting device can also be provided at the distal end of the catheter forceps, as shown in FIG. 10. In this embodiment, the cover (86) includes a number of segments, in this case three, that join together to make a sharpened tip when in a closed position shown in this figure. After the catheter forceps (85) is introduced into the bodily cavity and placed adjacent to the target tissue, the cover (86) is moved into an opened position (not shown) by an actuation mechanism (87) coupled to each of the cover sections (86). In the embodiment shown in FIG. 10, the actuation mechanism (87) is a piston positioned proximally to the sampling chamber (89). Each of the cover sections (86) is coupled to the piston (87) via a connector (88), such as a rod. The actuation mechanism (87) is actuated by supplying at least one of fluid and vacuum thereto from a fluid/vacuum source. When in the active position, the sections of the cover (86) open, or move outward from the center axis, forming a passage into the sampling chamber (89) provided at the distal end of the catheter forceps (85). As the catheter forceps (85) is pushed further into the tissue, parts of the tissue move into the sampling chamber (89) through the passage. A lumen (95) may be provided to supply vacuum to the sampling chamber (89) from the fluid/vacuum source to further draw the tissue sample into the chamber (89). Once enough tissue is collected, the sections of the cover (86) are moved back into the closed position, thereby cutting off the tissue sample and capturing it within the chamber (89) for withdrawal from the bodily cavity.

Figure 11:
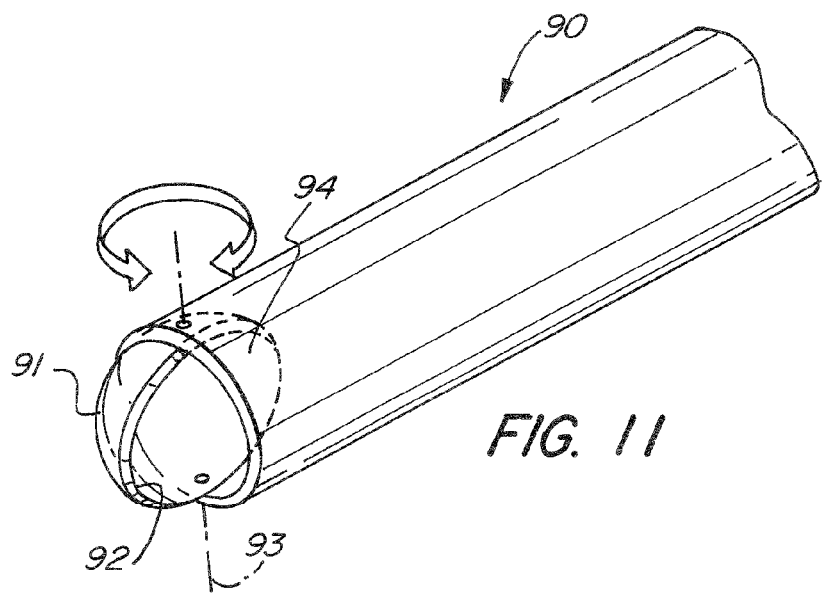
FIG. 11 is a perspective view of an exemplary embodiment of a pressure/vacuum actuated catheter forceps of the present invention.

In another advantageous embodiment shown in FIG. 11, the catheter forceps (90) include a half spherical cover (91) for the sampling chamber. The cover (91) has a sharpened knife-like edge (92) and turns about its center axis (93), as shown in FIG. 11. The cover (91) is opened by applying pressure to the actuation mechanism (not shown), and is closed when a vacuum is supplied. As the cover (91) closes, the supplied vacuum pulls the tissue sample into a half sphere space (94) of the spherical cover (91) and into the sampling chamber, as the tissue is being cut by the sharpened edge (92)

of the cover (91). As the half-spherical cover (91) is opened and closed by interchangeably supplying pressure and vacuum, tissue samples are cut off into the half sphere chamber (94) and suctioned into the sampling chamber.

Figure 12A:
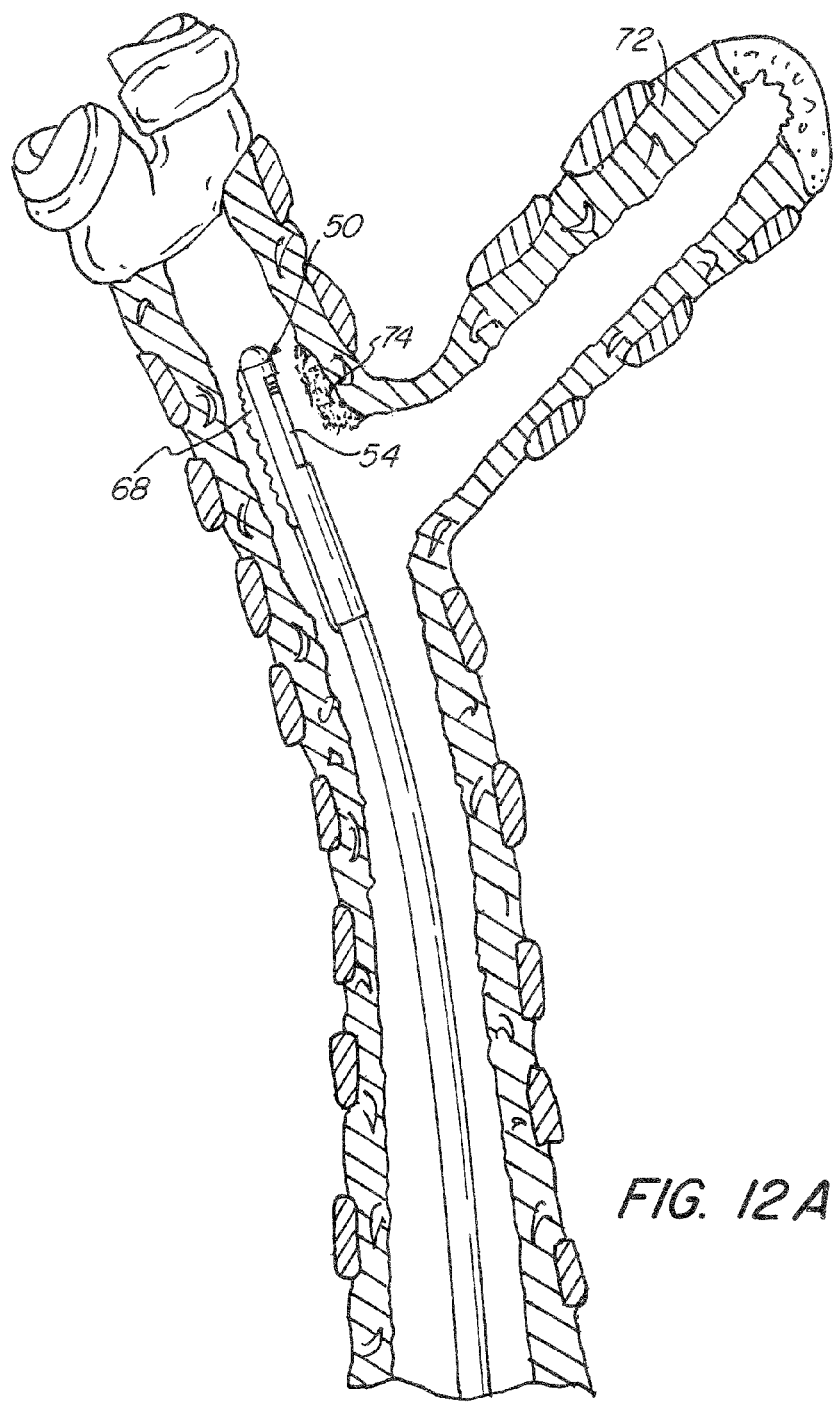
FIGS. 12A and 12B are cross-sectional views of the pressure/vacuum actuated catheter forceps of FIG. 6 being operated in a bodily cavity.
Figure 12B:
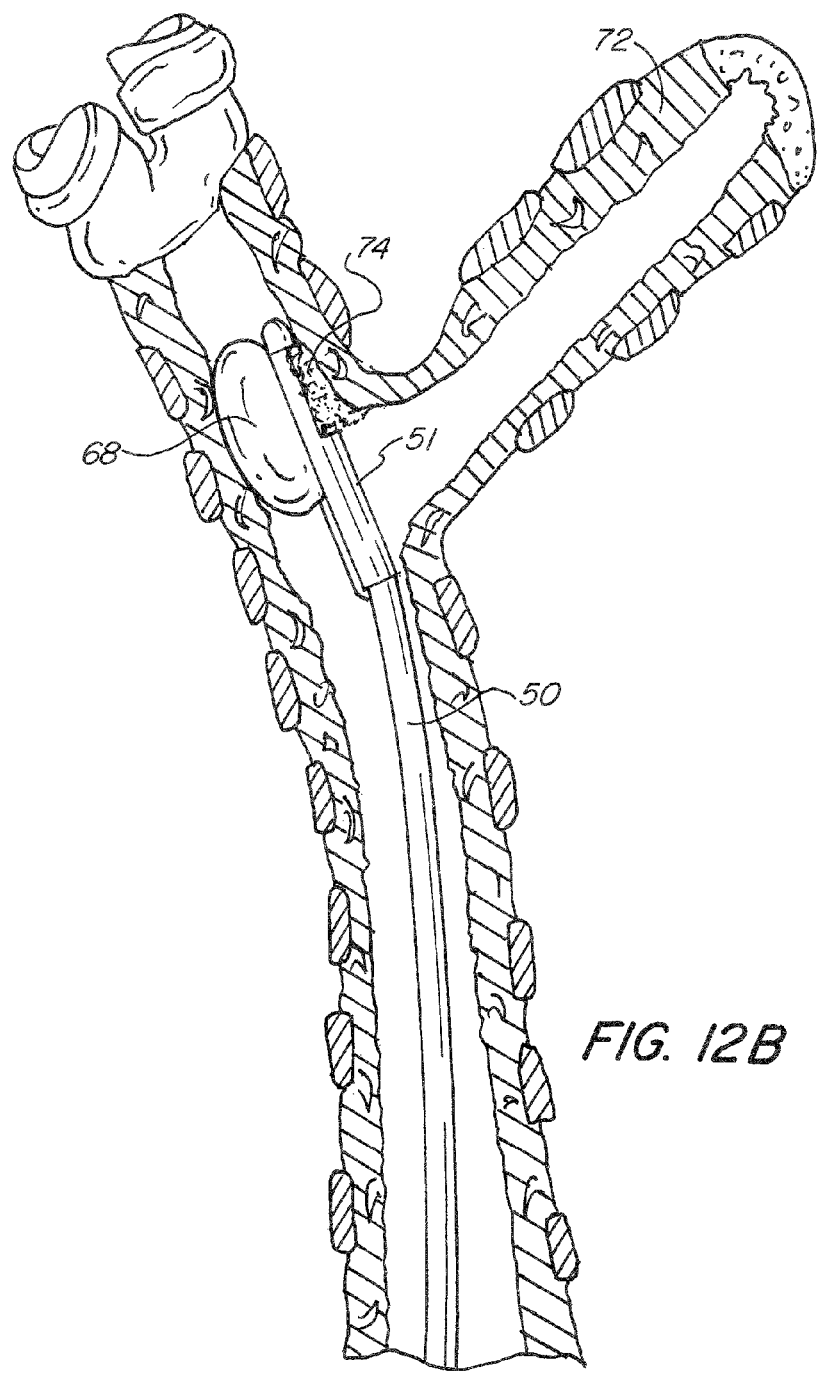

FIGS. 12A and 12B illustrate the use of the catheter forceps (50) with the inflatable balloon (68) inside a bodily cavity (72). First, the catheter forceps (50) is introduced into the patient's bodily cavity (72) and positioned adjacent to the target tissue (74), as shown in FIG. 12A. Then, the inflatable balloon (68) is inflated by supplying fluid thereto, such that it pushes the catheter (51) against the bodily cavity wall, thus positioning the catheter closer to the tissue (74) to be sampled, as shown in FIG. 12B. The sampling chamber cover is opened, and the tissue sample is resected and captured inside the sampling chamber by closing the chamber cover. The balloon (68) can then be rotated such that it is pressed against the resected tissue (74) to control the bleeding. Then, the balloon (68) is deflated by providing vacuum thereto and the catheter forceps (50) are withdrawn from the bodily cavity.

The catheter forceps of the present invention can be precisely positioned and actuated to sample indirect tissues, such as those positioned beyond the walls of an airway, lumen or vessel. The placement and actuation of the catheter forceps can be carried out under direct and/or indirect visualization.

Figure 13:
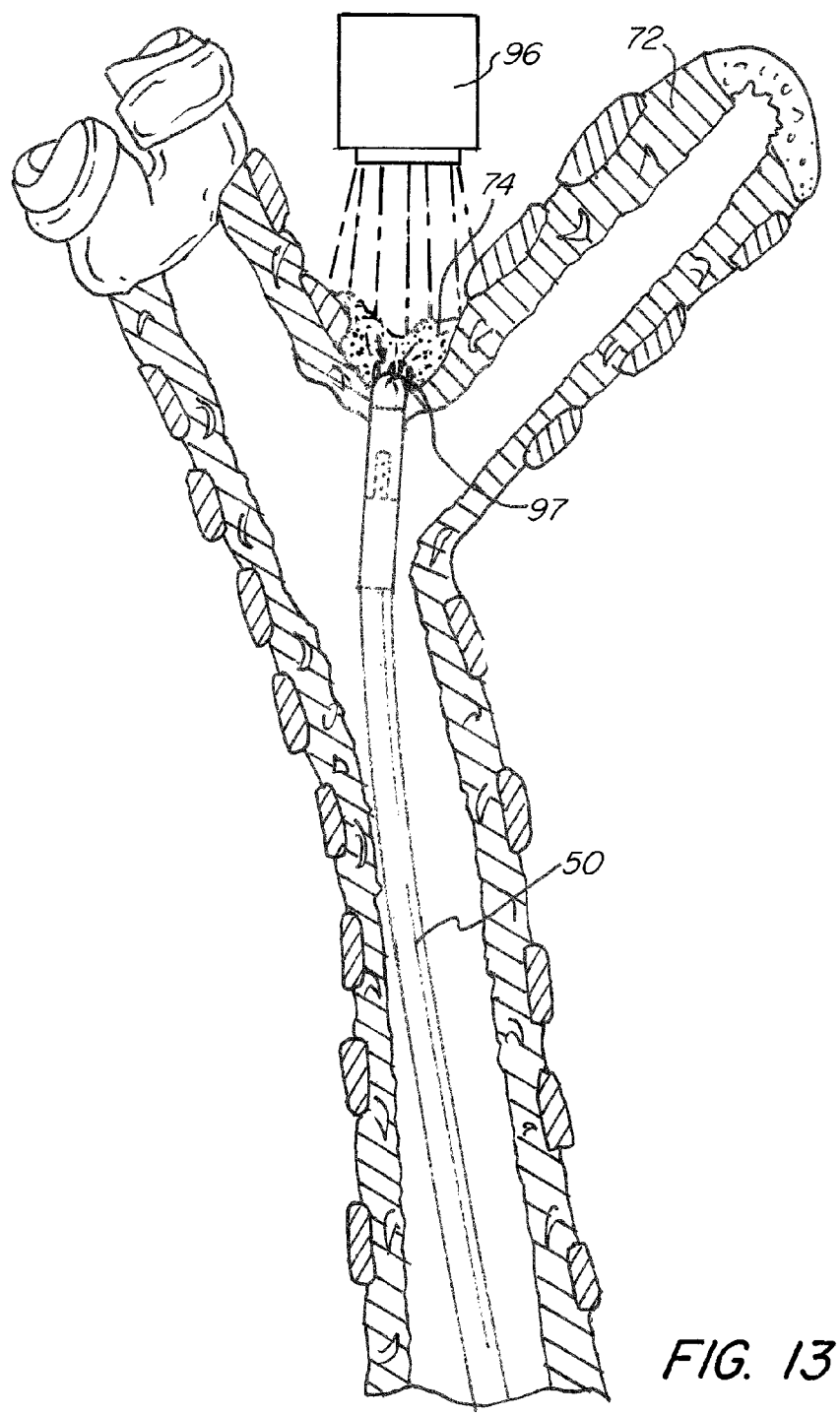
FIG. 13 is a cross-sectional view of the pressure/vacuum actuated catheter forceps of FIG. 10 being operated in a bodily cavity.

FIG. 13 illustrates actuation of the catheter forceps (50) under indirect visualization for sampling a tissue sample (74) located beyond the walls of a bodily cavity (72). This procedure is particularly suited for performing a transbronchial sampling of a lymph node tissue. The catheter forceps (50) is introduced into the bodily cavity (72) and guided toward the target tissue (74) positioned outside of the bodily cavity wall. The positioning of the catheter forceps (50) is monitored and visualized externally via an imaging modality (96), such as an ultrasound or x-ray device. The distal tip of the catheter forceps (50) includes imaging markers, e.g. radio opaque rings, that reflect the waves radiated by the imaging modality (96) to assist with the precise positioning of the catheter forceps (50) inside the bodily cavity (72). Once the catheter forceps (50) is positioned adjacent to the target tissue (74), the cutting device (97) disposed at the distal end of the forceps (50) is actuated to cut through the bodily cavity wall and into the tissue (74).

Figure 14:
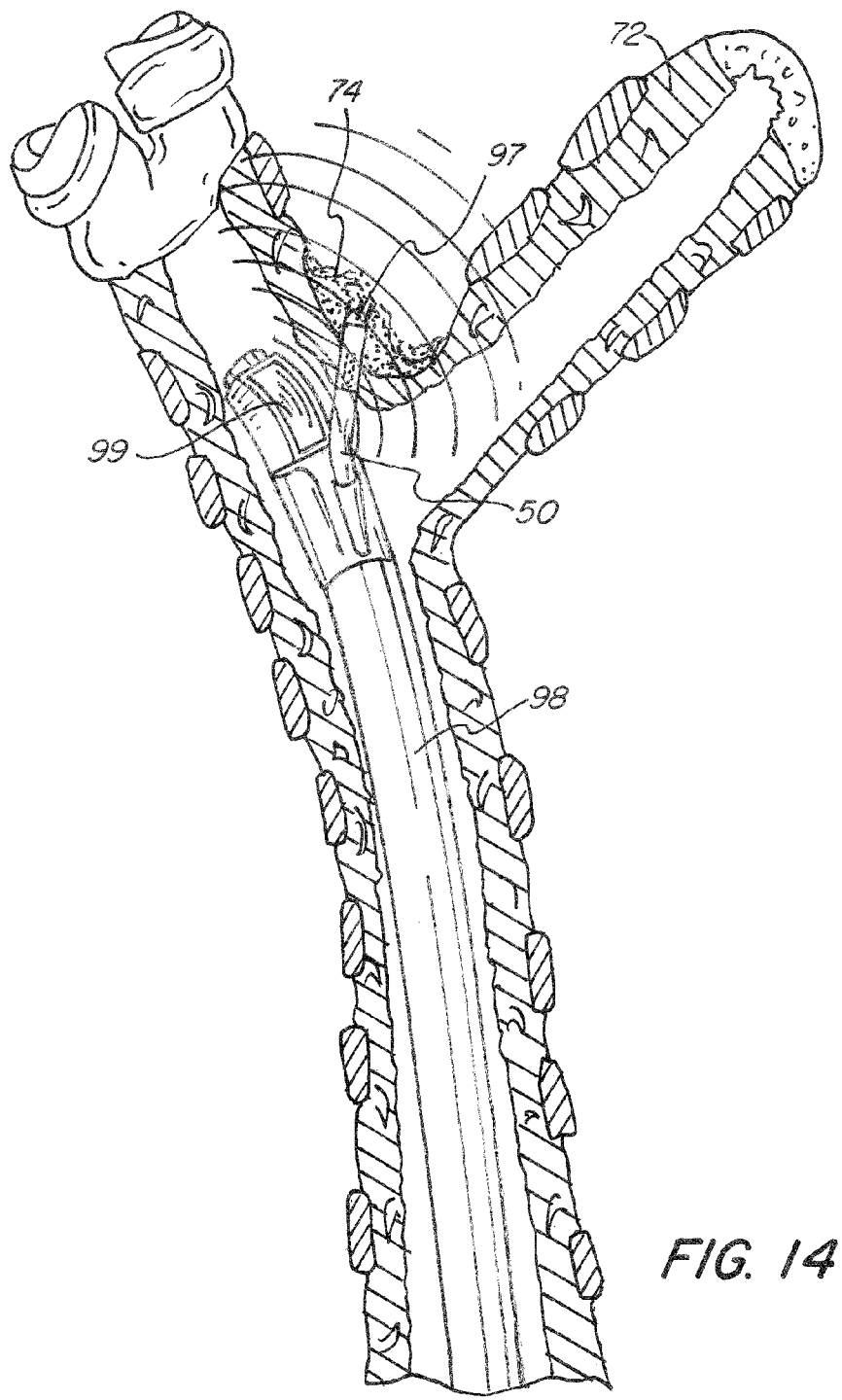
FIG. 14 is a cross-sectional view of the pressure/vacuum actuated catheter forceps of FIG. 10 being operated in a bodily cavity.

The positioning of the catheter forceps inside a bodily cavity can also be visualized internally, as shown in FIG. 14. In this embodiment, the forceps (50) is introduced into the bodily cavity (72) via a lumen in an endoscope (98). The endoscope (98) includes an imaging modality (99), e.g. an ultrasound device, positioned at the distal end of the endoscope (98). The imaging modality (99) emits waves, such as ultrasound waves, that reflect from the tissue (74) and the imaging markers provided on the forceps (50), as shown in FIG. 14, such that the precise positioning and operation of the forceps can be visualized and monitored. It is understood that other suitable internal and external imaging modalities can be used in accordance with the present invention. Additionally, in some embodiments, both the internal and external imaging modalities can be used to facilitate the positioning and actuation of the catheter forceps of the present invention.

The fluid supplied to the various catheter forceps lumens (28, 66, 70) may be gas or liquid. In certain advantageous embodiments, the fluid is a gas such as pressurized air. The fluid is supplied by a fluid source, such as an electro-magnetic pump. The pump may include an air compressor and a pressure tank, such as a Festo model CRVZS-0.1. The air pressure in the tank may be continuously monitored by a microcontroller which initiates the compressor to operate via an electrical signal output when the tank pressure drops below a certain pressure and displays the amount of air in the tank. A check valve, such as a Festo model H-1/8-A/1, may be located between the compressor and the tank in order to prevent the pressured gas from flowing back into the compressor. In another variation of the pump, the above-referenced compressor and pressure tank are not included, and the pressurized air or carbon dioxide is instead provided from an external source, such as gas tank or the operating room walls commonly found in an operating room.

In certain advantageous embodiments, a vacuum source, such as a Festo model VN-05-L-T3-PQ2-VQ2-R01-B, may also be included in the pump so that negative pressure can be applied to the lumens (28, 66, 70). The vacuum source may be turned on and off by a microcontroller via an electrical output signal.

In certain embodiments, a front panel of the pump includes an interface for a control device, such as a hand piece, further described below. The control device can be hardwired or wirelessly connected to the pump using readily available communication technologies, such as infrared or radio frequency (e.g., Bluetooth).

Figure 15:
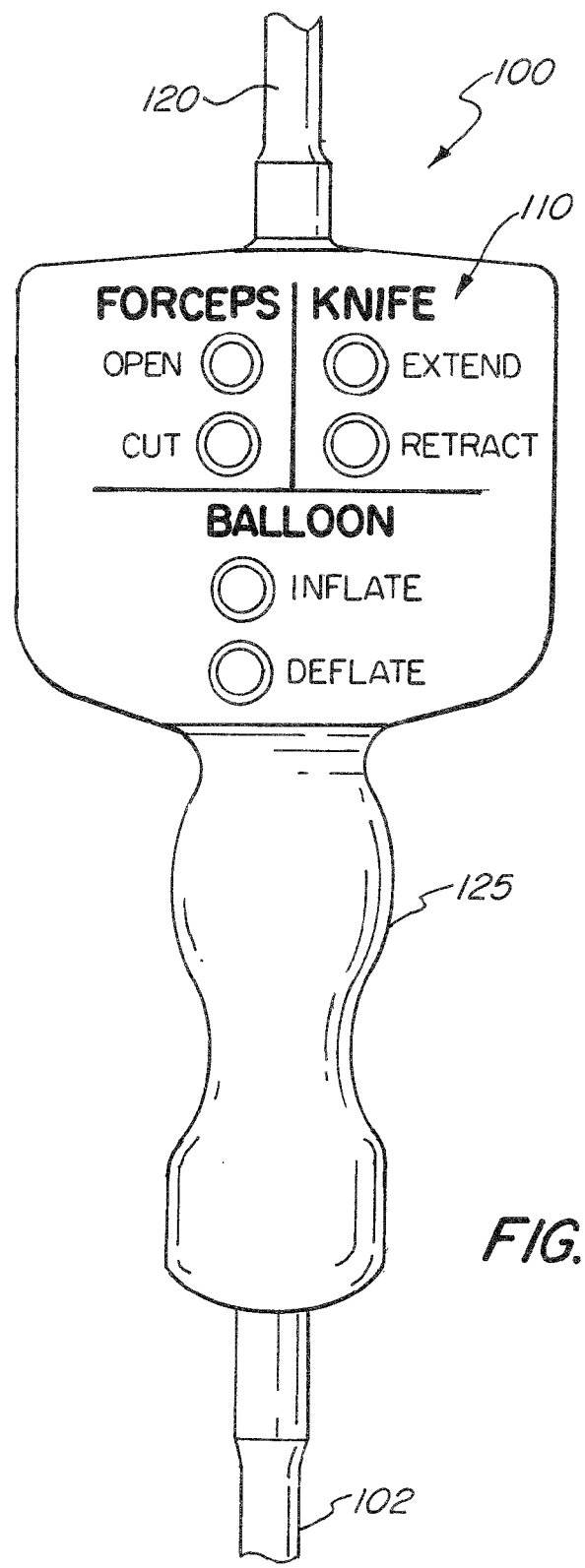
FIG. 15 is a front view of a control device used with the pressure/vacuum actuated catheter forceps of FIG. 1.

A proximal end of the catheter forceps typically includes a control device, such as a hand piece, for actuation of the forceps by a physician. An exemplary embodiment of the hand piece (100) is illustrated in FIG. 15. The hand piece (100) includes a connector (102) for connection to the proximal end of the catheter forceps and another connector (120) for connection to a fluid source, such as a pump. Any suitable type of connector can be used in accordance with the present invention.

The hand piece (100) further includes a plurality of control buttons (110). In the embodiment shown in FIG. 15, the hand piece (100) includes an "open" button that is used to supply fluid to the catheter forceps to open the movable cover of the sampling chamber, and a "cut" button that is used to provide vacuum to the forceps to close the cover and to cut the sample tissue. Additional buttons, such as "extend" and "retract" buttons shown in FIG. 15, can be included on the hand piece (100) to actuate the cutting device positioned at the distal end of the forceps. Further, buttons labeled as "inflate" and "deflate" are used to inflate and deflate the inflatable balloon provided on the catheter forceps.

The fluid and/or vacuum are supplied to the lumens (28, 66, 70) of the catheter forceps shown in FIG. 7A from a pump. The lumens (28, 66, 70) may be coupled to pressure ports (not shown), which control the flow of fluid from the fluid source to the lumens (28, 66, 70). It is appreciated that the hand piece (100) may include valves and valve control devices/electronics known in the art.

For example, microprocessor-controlled solenoid valves may be used to control the fluid flow and vacuum. Additionally, fluid pressure may be continuously monitored by a microcontroller using pressure regulators at the input from a tank, output of the regulator, and output to the lumens (66, 68, 70). Appropriate pressure regulators, such as, for example, Festo model SDET-22T-D10-G14-U-M12, provide to the microcontroller analog electrical signal (0V-10V) inputs that vary proportionally to the pressure at the regulators. The gas may pass through an electronic flow meter, such as a Festo model SFET-F010-L-WQ6-B-K1, and a filter, before being delivered to the lumens (66, 68, 70) the catheter forceps.

The hand piece (100) further includes a holding area (125) for gripping by the physician. The holding area is ergonomically shaped to facilitate comfortable gripping.

It should be understood that the hand piece can have any suitable configuration, and that the above configuration is not necessary for achieving the objects of the invention. It is further noted that, in some embodiments, some or all of the actuation commands can be executed via voice control instead of the buttons.

The catheter forceps of the present invention are advantageous over known prior art devices in that the forceps are miniaturized, low cost and disposable, intended to be deployed through working channels of various endoscopes and/or steerable catheters. The catheter forceps of the present invention are capable of obtaining biopsy tissue samples from the far reaches of the bodily lumens. The forceps parts can be advantageously made of molded plastic, such that the distal tip of the catheter forceps may be removed from the rest of the catheter to be sent for testing and subsequently discarded after the tissue sample is retrieved from the sampling chamber. The forceps part can be detached from the catheter portion via any suitable means, such as by unscrewing it, twisting it off, snapping it off, or simply cutting it off at a point after the rigid portion.

It would be appreciated by those skilled in the art that various changes and modifications can be made to the illustrated embodiment without departing from the spirit of the present invention. All such modifications and changes are intended to be covered hereby.

What is claimed is:

1. A method for extracting a tissue sample, comprising the steps of:
   inserting a catheter into a bodily cavity, said catheter comprising:
      a sampling chamber having an opening,
      a movable cover for closing the opening of said sampling chamber, and
      an actuation mechanism that moves said movable cover from an opened position, in which the opening of the sampling chamber is open, to a closed position, in which the opening of the sampling chamber is closed;
   positioning said sampling chamber next to tissue to be sampled;
   opening the opening of said sampling chamber by moving said movable cover to the opened position by providing a fluid to said actuation mechanism such that the fluid moves the movable cover into the opened position;
   drawing tissue sample into said sampling chamber and closing the opening of said sampling chamber by moving said movable cover to the closed position by supplying a vacuum that draws the sample into said sampling chamber while moving said movable cover from the opened position to the closed position; and
   withdrawing said catheter from the bodily cavity.

2. The method according to claim 1, wherein said catheter has a lumen in fluid communication with both said actuation mechanism and said sampling chamber for providing at least one of a fluid and a vacuum to said actuation mechanism and said sampling chamber.

3. The method according to claim 1, further comprising the step of cutting into the tissue to be sampled by actuating a cutting device positioned at the distal end of said catheter by providing at least one of a fluid and a vacuum.

4. The method according to claim 3, wherein said cutting device has an actuator, wherein the step of cutting into tissue comprises supplying a fluid to said actuator to position said cutting device in an activated position, in which the cutting device extends beyond the distal end of said catheter, and wherein the method further comprises the step of positioning said cutting device in an inactivated position, in which the cutting device does not extend beyond the distal end of said catheter, by supplying a vacuum to said actuator.

5. The method according to claim 4, wherein said catheter has a first lumen in fluid communication with both said actuation mechanism and said sampling chamber, and wherein the at least one of a fluid and a vacuum is provided via a second lumen in said catheter in fluid communication with said actuator.

6. The method according to claim 3, wherein said cutting device has an actuator, wherein the step of cutting into tissue comprises providing a vacuum to said actuator to position said cutting device in an activated position, in which the cutting device extends beyond the distal end of said catheter, and wherein the method further comprises the step of positioning said cutting device in an inactivated position, in which the cutting device does not extend beyond the distal end of said catheter, by supplying a fluid to said actuator.

7. The method according to claim 6, wherein the at least one of a fluid and a vacuum is provided to the actuator of said cutting device via a lumen in fluid communication with the actuator, said actuation mechanism and said sampling chamber.

8. The method according to claim 1, further comprising the step of inflating at least one inflatable balloon provided on an outer wall of said catheter opposite said sampling chamber to position said sampling chamber adjacent to the tissue to be sampled.

9. The method according to claim 8, wherein the step of inflating the at least one inflatable balloon comprises supplying a fluid thereto via a second lumen in said catheter.

10. The method according to claim 1, wherein the steps of supplying the vacuum and providing the fluid are controlled via a control device provided at a proximal end of said catheter.

11. The method according to claim 1, wherein the steps of supplying the vacuum and providing the fluid are performed by a pump in fluid communication with said lumen in said catheter.

12. The method according to claim 1, further comprising the step of opening said movable cover after said catheter is withdrawn from the bodily cavity to retrieve the tissue sample from said sampling chamber.

13. Catheter forceps for extracting a tissue sample, comprising:
   a catheter;
   a sampling chamber positioned at a distal end of said catheter, said sampling chamber having an opening and a movable cover for closing the opening; and
   an actuation mechanism that opens the opening of said sampling chamber by moving said movable cover to an opened position in response to a supply of fluid to said actuation mechanism such that said fluid moves the movable cover into the opened position, wherein said actuation mechanism both-supplies a vacuum to the sampling chamber to draw a tissue sample into the chamber while the vacuum closes the opening of said sampling chamber by moving the movable cover to a closed position.

14. The catheter forceps according to claim 13, wherein said catheter has a lumen in fluid communication with both said actuation mechanism and said sampling chamber for providing at least one of a fluid and a vacuum to said actuation mechanism and said sampling chamber.

15. The catheter forceps according to claim 14, wherein said lumen supplies a vacuum to said sampling chamber to draw tissue sample into said sampling chamber.

16. The catheter forceps according to claim 14, wherein said actuation mechanism comprises a piston positioned in an actuation chamber, and wherein the actuation chamber is in fluid communication with said lumen.

17. The catheter forceps according to claim 14, wherein fluid is supplied by a fluid source in fluid communication with said lumen.

18. The catheter forceps according to claim 17, wherein said fluid source further comprises a vacuum source.

19. The catheter forceps according to claim 17, wherein said fluid source is an electro-pneumatic pump.

20. The catheter forceps according to claim 13, wherein said fluid is a gas.

21. The catheter forceps according to claim 13, further comprising at least one inflatable balloon positioned on an outer wall of said catheter opposite said sampling chamber.

22. The catheter forceps according to claim 21, wherein said catheter has a lumen in fluid communication with both said actuation mechanism and said sampling chamber, and a second lumen in fluid communication with the at least one inflatable balloon for supplying fluid thereto.

23. The catheter forceps according to claim 13, further comprising a movable cutting device positioned at the distal end of said catheter.

24. The catheter forceps according to claim 23, wherein the cutting device comprises an actuator for moving the cutting device to an active position, in which the cutting device extends beyond the distal end of said catheter, and to an inactive position, in which the cutting device does not extend beyond the distal end of said catheter, by providing at least one of a fluid and a vacuum.

25. The catheter forceps according to claim 24, wherein said catheter has a lumen in fluid communication with said actuation mechanism, said sampling chamber, and the actuator of said cutting device.

26. The catheter forceps according to claim 24, wherein said catheter has a first lumen in fluid communication with both said actuation mechanism and said sampling chamber, and a second lumen in fluid communication with the actuator of said cutting device.

* * * * *